(12) United States Patent
Giovannone et al.

(10) Patent No.: US 10,702,482 B2
(45) Date of Patent: Jul. 7, 2020

(54) SLOW-RELEASE SOLID ORAL COMPOSITIONS

(71) Applicant: GNOSIS SPA, Milan (IT)

(72) Inventors: Daniele Giovannone, Frosinone (IT); Niccolò Miraglia, Desio (IT); Marco Berna, Desio (IT)

(73) Assignee: GNOSIS SPA, Milan (IT)

( * ) Notice: Subject to any disclaimer, the term of this patent is extended or adjusted under 35 U.S.C. 154(b) by 0 days.

(21) Appl. No.: 15/037,149

(22) PCT Filed: Nov. 6, 2014

(86) PCT No.: PCT/IB2014/065852
§ 371 (c)(1),
(2) Date: May 17, 2016

(87) PCT Pub. No.: WO2015/071806
PCT Pub. Date: May 21, 2015

(65) Prior Publication Data
US 2016/0287519 A1    Oct. 6, 2016

Related U.S. Application Data

(60) Provisional application No. 61/989,645, filed on May 7, 2014.

(30) Foreign Application Priority Data

Nov. 18, 2013   (IT) .............................. MI2013A1906

(51) Int. Cl.
| A61K 9/28 | (2006.01) |
| A61K 31/7076 | (2006.01) |
| A61K 31/519 | (2006.01) |
| A61K 9/20 | (2006.01) |
| A61K 31/205 | (2006.01) |
| A61K 31/714 | (2006.01) |
| A61K 45/06 | (2006.01) |

(52) U.S. Cl.
CPC .......... *A61K 9/2813* (2013.01); *A61K 9/2095* (2013.01); *A61K 9/282* (2013.01); *A61K 9/288* (2013.01); *A61K 31/205* (2013.01); *A61K 31/519* (2013.01); *A61K 31/7076* (2013.01); *A61K 31/714* (2013.01); *A61K 45/06* (2013.01); *A61K 9/2893* (2013.01)

(58) Field of Classification Search
None
See application file for complete search history.

(56) References Cited

U.S. PATENT DOCUMENTS

| 4,764,603 A * | 8/1988 | Zappia ................... C07H 19/16 536/27.3 |
| 8,329,208 B2 | 12/2012 | Harrison et al. |
| 2005/0181047 A1 | 8/2005 | Romero |
| 2009/0209543 A1* | 8/2009 | Valoti .................. C07D 475/04 514/249 |
| 2013/0133551 A1* | 5/2013 | Giovannone .......... A61K 47/44 106/214.2 |

FOREIGN PATENT DOCUMENTS

| JP | 2008-519071 | 6/2008 |
| WO | 03/043608 | 5/2003 |
| WO | 2006/052227 | 5/2006 |
| WO | 2007/113885 | 10/2007 |
| WO | 2010/009449 | 1/2010 |
| WO | 2011/012989 | 2/2011 |

OTHER PUBLICATIONS

Fukui et al. (International Journal of Pharmaceutics 216 (2001) 137-146 ).*
International Search Report dated Feb. 19, 2015 in corresponding PCT Application No. PCT/IB2014/065852.
Nelson et al., "Effects of Magnesium Stearate on Tablet Properties", Jul. 23, 2009; as stated in the ISR "Retrieved from the Internet: URL: http://www.osd.rutgers.edu/gs/09papers/PharmaDC.pdf"; 9 pages.
Dürig et al., "Mechanistic Evaluation of Binary Effects of Magnesium Stearate and Talc as Dissolution Retardants at 85% Drug Loading in an Experimental Extended-Release Formulation", Journal of Pharmaceutical Sciences, Oct. 1997, vol. 86, No. 10, pp. 1092-1098.

(Continued)

Primary Examiner — Patricia Duffy
Assistant Examiner — Garen Gotfredson
(74) Attorney, Agent, or Firm — Wenderoth, Lind & Ponack, L.L.P.

(57) ABSTRACT

The present invention relates to a slow-release solid oral nutraceutical and/or pharmaceutical composition comprising: a core containing a donor of methyl groups and at least one pharmaceutically acceptable excipient, and an outer coating containing shellac and/or a pharmaceutically acceptable salt thereof, magnesium stearate, and at least one pharmaceutically acceptable excipient. The coating of said solid oral composition allows the donor of methyl groups, preferably SAMe and/or a pharmaceutically acceptable salt thereof, to cross intact the gastric barrier and release the same in a continuous and complete manner along the entire digestive tract.

15 Claims, 5 Drawing Sheets

(56) References Cited

OTHER PUBLICATIONS

Mischoulon et al., "Role of S-adenosyl-$_L$-methionine in the treatment of depression: a review of the evidence", The American Journal of Clinical Nutrition, 2002, vol. 76(suppl), pp. 1158S-1161S.

McMillan et al., "S-adenosyi-$_L$-methionine: transcellular transport and uptake by Caco-2 cells and hepatocytes", Journal of Pharmacy and Pharmacology, 2005, vol. 57, pp. 599-605.

\* cited by examiner

SLOW-RELEASE SOLID ORAL COMPOSITIONS

The present invention relates to a slow-release solid oral nutraceutical and/or pharmaceutical composition comprising:
a) a core containing a donor of methyl groups and at least one pharmaceutically acceptable excipient, and
b) an outer coating containing shellac and/or a pharmaceutically acceptable salt thereof, magnesium stearate, and at least one pharmaceutically acceptable excipient.

The coating of said solid oral composition allows the donor of methyl groups, preferably SAMe and/or a pharmaceutically acceptable salt thereof, to cross intact the gastric barrier and release the same in a continuous and complete manner along the entire digestive tract.

STATE OF THE ART

S-adenosyl-L-methionine (SAMe) is present in all living organisms, where it plays the role of the most important methylating agent in cell metabolisms.

In the human organism, the deficiency of this important molecule contributes to the onset of several diseases, such as the development of osteoarthritis, liver cirrhosis, cystic fibrosis, certain depressive states, senile diseases such as Alzheimer's and Parkinson's diseases. Reduced levels of SAMe are also to be connected with the development of cardiovascular and neurological disorders, both presumably to be connected to an increase of homocysteine in the plasma. This molecule exists in two diastereomeric forms: (S,S)—S-adenosyl-L-methionine and (R,S)—S-adenosyl-L-methionine, of which only the first one is the biologically active form.

The inherent instability of the molecule, i.e. its tendency to racemise and its chemical instability at temperatures above 0° C., has long limited the use of exogenous SAMe in cases where its integration in the diet would be necessary.

SAMe is mainly administered by oral route. SAMe solid oral formulations, in the form of coated tablets and capsules, have allowed to overcome other obstacles to its use, such as the irritating activity exerted by SAMe on the mucous membranes, and the masking of the unpleasant taste.

Film-coated tablets, whose solubility is pH-dependent, are widely used in the market. Many of these involve the use of film-formers based on polymers of acrylic or methacrylic acid, such as for example Eudragit™ that offers excellent resistance to the gastric environment and ensures, at the same time, a rapid and complete dissolution in a neutral-basic environment such as the bowel. However, Eudragit™ is not to date accepted as a coating for nutritional products, as opposed to what happens in the pharmaceutical field.

One of the main drawbacks associated with the oral use of SAMe is the high dosage required for the treatment: the doses normally suggested for the products on the market correspond to 800-1600 mg of SAMe ion per day, often administered in several daily doses consisting of fractions of the total daily dose. In a series of clinical studies, the effect of SAMe has been demonstrated for doses of 200-1600 mg/day (Mischoulon D et al., Am. J. Clin. Nutr. 76 (5), 1158S-2002). The use of such a high dose is necessary to counteract a rather poor oral bioavailability in spite of the high solubility of the molecule. In vitro cellular uptake studies in Caco-2 cells cultures report how the poor oral bioavailability shown by SAMe can be correlated to absorption problems of the molecule, rather than to its rapid metabolism (McMillan et al., J. Pharm. Pharmacol. 57, 599-2005).

All this shows how SAMe oral absorption is a timely problem, and how useful all the solutions that increase the absorbed fraction can be.

In the prior art, some solutions have been implemented in an attempt to design oral formulations that control and optimise SAMe release from a tablet and, therefore, its intestinal adsorption.

The U.S. Pat. No. 8,329,208 describes a double-coating formulation, in order to improve SAMe release profile, and to release the maximum amount of the molecule in the environment within a specific pH window, corresponding to a specific portion of the digestive system.

The formulation provides a dissolution of the film of up to 90% within 60 minutes at pH 6.0, thus at a value lower than the usual pH 6.8 provided by the pharmacopoeias for standard enteric coatings.

However, extensive evidence in the literature shows how SAMe is actually absorbed in different sectors of the gastrointestinal tract, at different levels of efficiency, including the buccal mucosa. These findings tend to suggest that it is not possible to delimit the absorbing function of SAMe to a small section of the digestive system.

The international patent applications WO2011/012989 and WO2010/009449 describe the preparation of tablets containing SAMe, coated with a film that provides the tablets with extended-release characteristics.

In WO2010/009449, SAMe release occurs in a constant manner, independently from the pH of the environment, up to a maximum of 60-80% of SAMe within 16-18 ore. The release of the active principle is, therefore, not complete and occurs in a too long period of time. It is actually known that, 12 hours after ingestion, a product reaches the colon where the absorption of most substances is minimal.

On the other hand, WO2011/012989 sets out a number of different solutions aimed at increasing the fraction of SAMe adsorbed, mainly by maximising the period of residence of SAMe in the gastrointestinal tract, or by adding modulators of the tight junctions that contribute to weaken these cellular structures that limit the diffusion of molecules in the epithelium, through the paracellular space. However, a coating or a formulation able to ensure a continuous release of SAMe along the entire intestinal tract is never described.

Furthermore, in these two patent applications, the dissolution profiles do not exhibit the characteristics of a gastric resistance, i.e. a percentage of SAMe release lower than 10% in the first two hours of incubation at pH 1.2.

It is, therefore, felt the need for a gastroresistant oral formulation that ensures a complete and continuous release of SAMe with a maximum absorption in the digestive system.

DESCRIPTION

Figure 1:
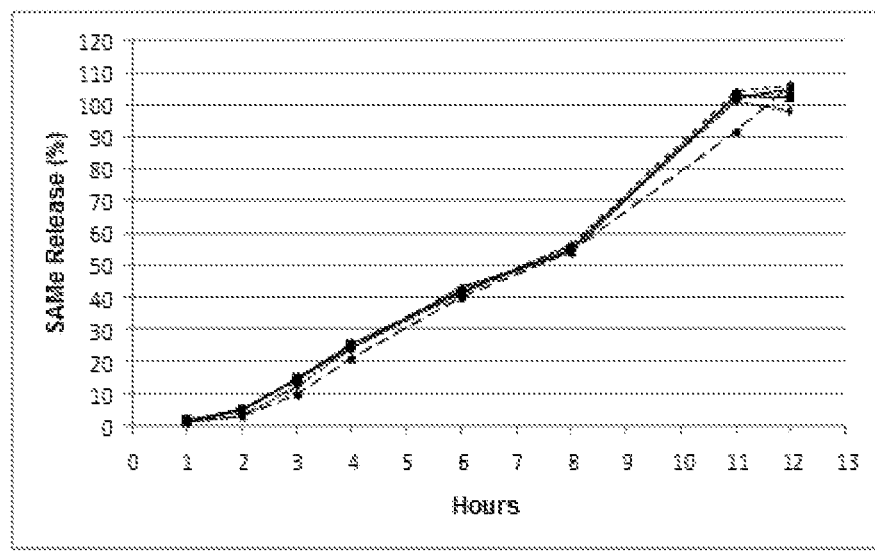
FIG. 1: Dissolution profile for 6 tablets: 0-2 hours: gastric buffer pH 1.2; 2-12 hours: duodenal buffer pH 6.8

A composition, comprising shellac and magnesium stearate, has now surprisingly been found that, applied as a coating to solid oral formulations of SAMe, ensures in a single solution gastric resistance and linear kinetic release (order 0), in the entire intestinal tract over 12 hours, i.e. corresponding to the time of residence of the molecule in the intestinal tract useful for the absorption of substances ingested.

This coating consists of a single film which simultaneously provides the described pharmacokinetic characteristics, and a coating able to ensure the stability of the molecule, without the need for a dual film-coating.

A similar release kinetics (order 0) is, therefore, able to ensure a quantity of SAMe in the digestive tract within a range of concentrations defined as therapeutic window over the 10 hours after the crossing of the gastric compartment. This allows a single daily administration of SAMe, with the maximum therapeutic effectiveness, in contrast to what reported in the prior art.

Therefore, a first object of the present invention is a slow-release solid oral nutraceutical and/or pharmaceutical composition comprising:
a) a core containing a donor of methyl groups and at least one pharmaceutically acceptable excipient, and
b) an outer coating containing shellac and/or a pharmaceutically acceptable salt thereof, magnesium stearate, and at least one pharmaceutically acceptable excipient.

Preferably, said composition consists of:
a) a core containing a donor of methyl groups and at least one pharmaceutically acceptable excipient, and
b) an outer coating containing shellac and/or a pharmaceutically acceptable salt thereof, magnesium stearate, and at least one pharmaceutically acceptable excipient.

Therefore, according to a preferred embodiment, the above mentioned composition contains a single outer coating, i.e. it does not include additional coatings between the core and the above mentioned outer coating.

According to the present invention, said solid oral composition is selected from direct mixture, tablet, capsule and granule, preferably is a tablet.

According to the present invention, with the term "slow-release" is meant a delayed-, extended-, and controlled-release.

According to the present invention, with the term "donor of methyl groups" is meant a compound capable of transferring a methyl group to other acceptor compounds in the context of metabolic reactions, such metabolism being generally known as one-carbon metabolism.

According to the present invention, a donor of methyl groups is selected from SAMe or a pharmaceutically acceptable salt thereof, trimethylglycine, dimethylglycine, vitamin B12, a folate, a reduced folate or a mixture thereof preferably is selected from SAMe, a pharmaceutically acceptable salt thereof, a reduced folate or a mixture thereof.

According to the present invention, with the term "reduced folate" is meant a derivative of folic acid (folate), having a lower oxidation state of the corresponding folate due to the reduction of a portion of the pteridine ring, being the compounds listed below an example with the exception of folic acid.

According to the present invention, examples of suitable folate and reduced folate are: folic acid, (6S)-5-methyltetrahydrofolic acid [(6S)-5-MTHF] or a pharmaceutically acceptable salt thereof. According to the present invention, a preferred reduced folate is a salt of (6S)-5-methyltetrahydrofolic acid.

According to the present invention, particularly preferred examples of (6S)-5-MTHF salts are (6S)-5-MTHF calcium salt, (6S)-5-MTHF glucosamine salt, or (6S)-5-MTHF galactosamine salt.

Said pharmaceutically acceptable salt of SAMe is selected from S-adenosylmethionine sulfate p-toluensulfonate, S-adenosylmethionine 1,4-butanedisulfonate, S-adenosylmethionine sulfate, S-adenosylmethionine tosilate or S-adenosylmethionine phytate, preferably said pharmaceutically acceptable salt of SAMe is selected from sulfate p-toluensulfonate or 1,4-butanedisulfonate.

Preferably, SAMe or a pharmaceutically acceptable salt thereof is present in the composition of the invention in an amount ranging between 50% and 90% by weight, preferably between 60% and 85% by weight, based on the total weight of the composition.

Pharmaceutically acceptable excipients that can be used in the core a) of the composition of the present invention are selected from diluents, lubricants, binders, glidants, adsorbents, thickeners, alkalizings, plasticizers, and mixtures thereof.

Preferably, said binder is microcrystalline cellulose, said alkalizings are selected from magnesium hydroxide, calcium oxide and mixtures thereof, said lubricants are selected from stearic acid, magnesium stearate and mixtures thereof, said glidant or adsorbent is precipitated silica, said diluents are selected from mannitol, calcium sulfate dihydrate and mixtures thereof, said thickener is sodium alginate, said plasticizers are selected from polyethylene glycol, triethyl citrate and mixtures thereof.

According to the present invention, the outer coating b) is preferably a gastroresistant coating. Said coating comprises shellac or a pharmaceutically acceptable salt thereof, magnesium stearate, and at least one pharmaceutically acceptable excipient.

According to the present invention, preferred shellac salts are selected from arginine salt, ammonium salt, boron salt and potassium salt.

More preferably said shellac salt is arginine salt.

According to the present invention, the shellac or a pharmaceutically acceptable salt thereof is in the form of a solution, preferably in the form of an aqueous solution or an alcoholic solution, more preferably in the form of an aqueous solution.

Preferably, the shellac or a pharmaceutically acceptable salt thereof is present in the composition of the invention in an amount ranging between 0.5% and 10% by weight, more preferably between 1% and 5% by weight, based on the total weight of the composition.

Shellac is the purified product of lac, a natural resin oligomer with a molecular weight of about 1000 D, secreted by the parasite insect *Kerria lacca*, and is currently commercially available under the brand Shellac™ (marketed by SSB).

According to a preferred embodiment, magnesium stearate is present in the composition of the invention in an amount ranging between 0.1% and 2% by weight, preferably between 0.2% and 1% by weight, based on the total weight of the composition.

According to another preferred embodiment, magnesium stearate is present in the outer coating b) in an amount ranging between 5% and 30% by weight, preferably between 10% and 20% by weight, based on the total weight of the outer coating b).

Pharmaceutically acceptable excipients that can be used in the outer coating b) of the present invention are selected from lubricants, diluents, plasticizers, thickeners, stabilizers, and mixtures thereof.

Preferably, said lubricant is magnesium stearate, said diluents are selected from titanium dioxide, talc and mixtures therefor, said plasticizers are glycerol and triethyl citrate, said thickener is sodium alginate.

According to a more preferred embodiment of the present invention, pharmaceutically acceptable excipients that can be used in the outer coating b) are selected from magnesium stearate, titanium dioxide, talc, glycerol, and mixture thereof.

The solid oral composition according to the invention is characterised in that no more than 10% of the donor of methyl groups is released in the first two hours and the remaining 90% is released in the following nine hours, according to a zero order kinetic release.

As it can be seen in FIG. 1, the solid oral composition according to the present invention is able to cross intact the gastric barrier and to release the active principle in a delayed and continuous manner.

Furthermore, the solid oral composition according to the present invention is stable and about 20 times less hygroscopic than conventional solid formulations, as shown in Table 1.

TABLE 1

| Known tablets based on SAMe SAMe tablet 400 mg K. F. % T = 0 | Known tablets based on SAMe SAMe tablet 400 mg K. F. % T = 24 h* | Tablets (Example 1) K. F. % T = 0 | Tablets (Example 1) K. F. % T = 24 h* |
| --- | --- | --- | --- |
| Batch 01 1.24 | 3.44 | 1.32 | 1.76 |
| Batch 02 1.21 | 3.87 | 1.23 | 1.68 |
| Batch 03 1.10 | 3.77 | 1.21 | 1.76 |
| Batch 04 1.33 | 3.56 | 1.32 | 1.62 |
| Batch 05 1.39 | 3.90 | 1.33 | 1.34 | at 40° C., 75% RH (Relative Humidity) K.F. (water content determination according to Karl Fischer method)

T=time

A further object of the present invention is a process for the preparation of said slow-release solid oral composition, comprising the following steps:
a) mixing a donor of methyl groups with at least one pharmaceutically acceptable excipient;
b) pre-compression, followed by granulation, of the mixture obtained in step a);
c) mixing the granulated material obtained in step b) with at least one pharmaceutically acceptable excipient;
d) film-coating the solid oral form obtained in step c) with an aqueous phase containing shellac and/or a pharmaceutically acceptable salt thereof, magnesium stearate, and at least one pharmaceutically acceptable excipient.

The process according to the present invention is performed in an environment with a relative humidity lower than 20%, and the temperature is maintained between 18 and 25° C., preferably at about 20° C.

According to the present invention, in step a) the donor of methyl groups is mixed with pharmaceutically acceptable excipients selected from diluents, lubricants, glidants, adsorbents, thickeners, alkalizings, plasticizers, and mixtures thereof.

Preferably, said pharmaceutically acceptable excipients are selected from calcium sulfate dihydrate, magnesium oxide, sucrose, microcrystalline cellulose, hydrogenated fat acids, magnesium stearate, glycerol behenate, precipitated silica, magnesium hydroxide, calcium oxide, polyalcohols, talc, sodium alginate, glycerol, polyethylene glycol, triethyl citrate, triacetin, and mixtures thereof.

More preferably, in step a), the donor of methyl groups is mixed with an excipient selected from calcium oxide, magnesium hydroxide, magnesium stearate, precipitated silica, and mixtures thereof.

Even more preferably, in step a), the donor of methyl groups is mixed with calcium oxide, magnesium hydroxide, magnesium stearate and precipitated silica.

In the above mentioned mixture, magnesium hydroxide is present in an amount ranging between 1% and 10% by weight, magnesium stearate is present in an amount ranging between 0.5% and 5% by weight, and/or precipitated silica is present in an amount ranging between 0.1% and 0.5% by weight.

These percentages by weight are to be understood with respect to the weight of the donor of methyl groups.

Preferably, the donor of methyl groups in step a) is selected from SAMe or a pharmaceutically acceptable salt thereof, trimethylglycine, vitamin B12, a folate, a reduced folate or a mixture thereof, more preferably is selected from SAMe, a pharmaceutically acceptable salt thereof, a reduced folate or a mixture thereof.

According to the present invention, the granulated material obtained in step b) is mixed with pharmaceutically acceptable excipients selected from binders, lubricants, plasticizers and mixtures thereof.

Preferably, in step c), the granulated material is mixed with an excipient selected from microcrystalline cellulose, hydrogenated fat acids, magnesium stearate, glycerol behenate and mixtures thereof.

More preferably, in step c), the granulated material is mixed with microcrystalline cellulose, hydrogenated fat acids, magnesium stearate, glycerol behenate In the above mentioned mixture, microcrystalline cellulose is present in an amount ranging between 1% and 20% by weight, hydrogenated fat acids are present in an amount ranging between 1% and 15% by weight, magnesium stearate is present in an amount ranging between 0.5% and 5% by weight and glycerol behenate is present in an amount ranging between 1% and 5% by weight.

These percentages by weight are to be understood with respect to the weight of the donor of methyl groups.

According to the present invention, the solid oral form obtained in step c) is then film-coated with an aqueous phase containing shellac and/or a pharmaceutically acceptable salt thereof, magnesium stearate, and eventually a pharmaceutically acceptable excipient.

Subsequently, magnesium stearate and some pharmaceutically acceptable excipients selected from stearic acid, sodium alginate, ethyl cellulose, zein, titanium dioxide, talc, triethyl citrate, PVP, hydroxypropyl cellulose, and mixture thereof, are added.

According to the invention, during the film-coating step, the temperature of the core containing the active principle is maintained at a temperature ranging between 30° C. and 60° C., preferably between 40° C. and 55° C., more preferably at about 48° C.

Preferably, said temperature is maintained for a period of time ranging between 10 minutes and 2 hours, more preferably for about 1 hour.

According to a preferred embodiment of the present invention, the temperature of the core is subsequently lowered to reach a temperature ranging between 40° C. and 50° C., more preferably about 44° C., in the step following the polymerisation of the film.

The composition according to the present invention can be used in the treatment of depressive states, as hepatoprotector, as adjuvant therapy in the treatment and prevention of inflammatory states of joints and articulations.

According to the present invention, with the term "adjuvant therapy" is meant a treatment which is carried out simultaneously or after the main medical action, and without any indication that there are residues of the disease.

Figure 2:
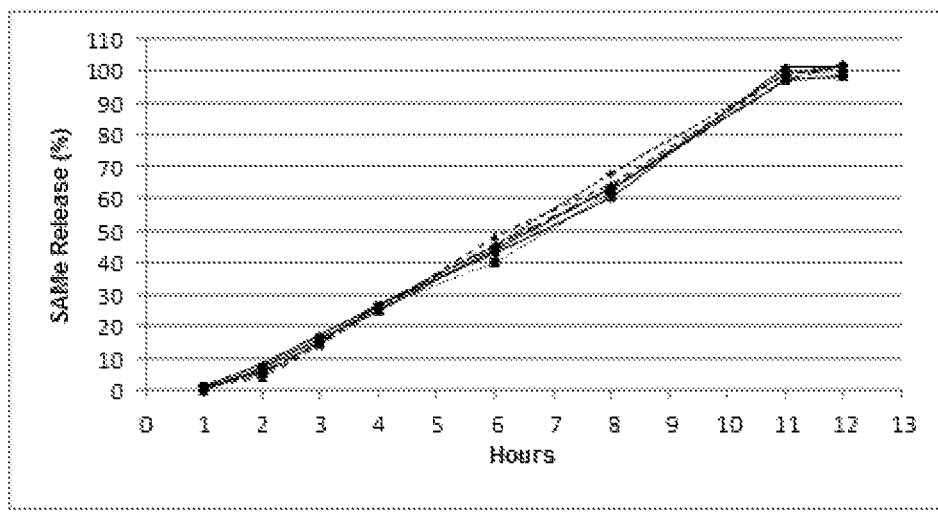
FIG. 2: Dissolution profile for 6 tablets of batch 004 at T=0 and at T=6 months (stress test): 0-2 hours: gastric buffer pH 1.2; 2-12 hours: duodenal buffer pH 6.8
Figure 2:
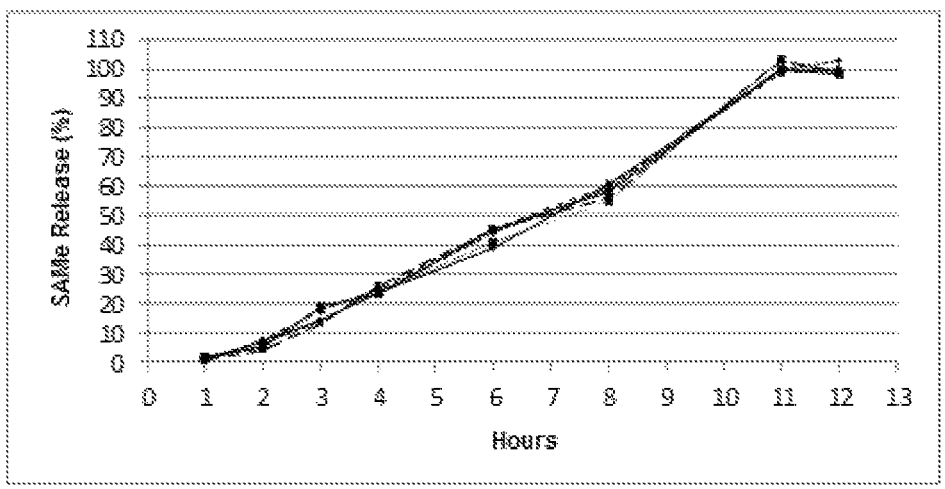
Figure 3:
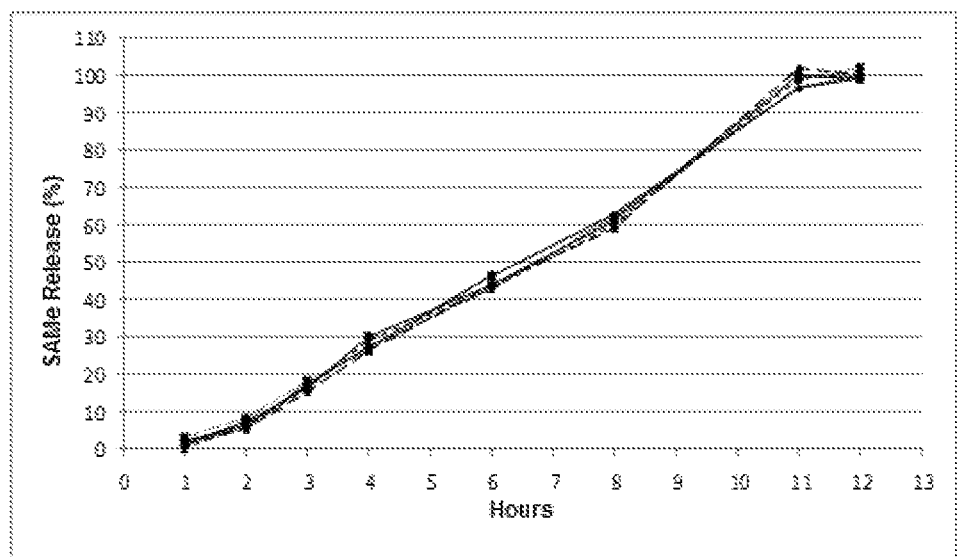
FIG. 3: Dissolution profile for 6 tablets of batch 015 at T=0 and at T=12 months (shelf life): 0-2 hours: gastric buffer pH 1.2; 2-12 hours: duodenal buffer pH 6.8
Figure 3:
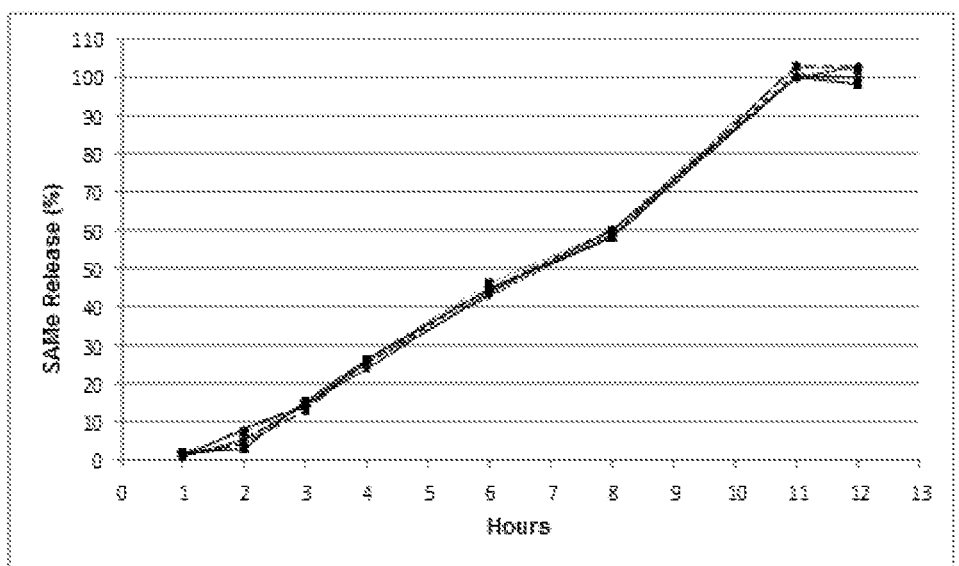

Moreover, as it can be appreciated in FIGS. 1-3, said composition allows to prolong the release of SAMe or a salt thereof, through the use of an outer coating, preferably gastroresistant, comprising shellac or a pharmaceutically acceptable salt thereof, and magnesium stearate.

Therefore, a further object of the present invention is the use of an outer coating comprising shellac or a pharmaceutically acceptable salt thereof, and magnesium stearate to prolong the release of a donor of methyl groups, preferably SAMe.

EXAMPLES

Example 1

Tablets Containing 400 mg of SAMe Ion/Tablet

Composition Based on SAMe Sulfate p-Toluensulfonate

| | |
|---|---|
| SAMe sulfate p-toluensulfonate | 800.00 mg |
| Core: | |
| Magnesium oxide | 40.0 mg |
| Magnesium hydroxide | 100.00 mg |
| Stearic acid | 120.00 mg |
| Magnesium stearate | 20.00 mg |
| Precipitated silica | 5.00 mg |
| Total weight of the core | 1085.00 mg |
| Coating: | |
| Shellac | 15.00 mg |
| Arginine | 3.00 mg |
| Magnesium stearate | 6.0 mg |
| Titanium dioxide | 5.00 mg |
| Talc | 15.00 mg |
| Glycerol | 5.00 mg |
| Tablet total weight | 1134.50 mg |

1.1. Mixing

The working environment is conditioned at a temperature of 20° C. and at a relative humidity value of about 20% RH. SAMe sulfate p-toluensulfonate, magnesium oxide, magnesium hydroxide, stearic acid and 50% of the magnesium stearate, in the amounts listed above, are then transferred into the mixer, keeping under stirring for about 20 minutes. Upon completion of this operation, the resulting mixture is transferred into dry containers, always under controlled humidity and temperature.

1.2. Pre-Compression

The mixture is then pre-compressed using a rotary tableting machine equipped with 22.0 mm round punches. The hardness of the tablets produced should be regulated in order to subsequently produce a granulate material with good rheological properties.

1.3 Granulation

The tablets produced during the first processing stage are granulated through a 1000-2000 μm mesh under a controlled humidity environment.

1.4 Mixing

The granulate material obtained in step 1.3 is transferred into the mixer, with the addition of precipitated silica and 50% of the magnesium stearate, and keeping under stirring for about 20 minutes. Upon completion of said operation, the resulting mixture is transferred into dry containers.

1.5 Compression

The final compression of the granulate material is performed by means of a rotary tableting machine equipped with oblong punches. The produced tablets have a hardness of between 20 and 33 Kp.

The stability tests on the uncoated tablets were only carried out at 40° C. and 75% RH, over a period of three months, and for a single batch, since they were not a finished product. The samples were stored in Alu/Alu blister packs.

TABLE 2

Batch 001 - core containing 400 mg of SAMe ion/tablet
(qualitative/quantitative composition as in Example 1)

| Batch (T/t)[1] | Water Content % (K. Fischer) | AD[2] (%) | MTA[3] (%) | SAMe[4] |
|---|---|---|---|---|
| 001 (40/0) | 1.36 | 0.43 | 0.54 | 405.65 |
| 001A (40/1) | 1.46 | 0.89 | 0.57 | 404.38 |
| 001B (40/3) | 1.47 | 1.34 | 1.38 | 402.32 |

[1]Temperature (° C.)/time (months);
[2]adenosine;
[3]methylthioadenosine;
[4]SAMe sulfate p-toluensulfonate (mg/tablet);

The data in Table 2 show that the tablets have good stability.

Tablet Filming

Arginine and shellac are solubilised at room temperature, in a container of appropriate size, to obtain a 20% w/v solution and, under continuous stirring, magnesium stearate, talc and silica are slowly added.

In another steel container, also equipped with a stirrer, sodium alginate is solubilised under vigorous stirring. The resulting suspension is poured into the solution of shellac, and the flask is rinsed with deionised water.

In the first coating step, the temperature of the cores is maintained at 48° C. for about 60 minutes, subsequently, and at regular intervals, it is lowered until it reaches a value of 44° C. in the final stage.

In the tablets thus produced, no increase in the water content percentage was observed. In addition, all the tests required by the quality specifications and the dissolution test, to verify the release profile over time, were performed on them.

Example 2

Tablets Containing 400 mg of SAMe Ion/Tablet

Composition Based on SAMe Sulfate n-Toluensulfonate

| SAMe sulfate p-toluensulfonate | 800.00 mg |
|---|---|
| Core: | |
| Microcrystalline cellulose | 100.0 mg |
| Magnesium hydroxide | 100.00 mg |
| Stearic acid | 120.00 mg |
| Magnesium stearate | 20.00 mg |
| Precipitated silica | 5.00 mg |
| Total weight of the core | 1145.00 mg |
| Coating: | |
| Shellac | 15.00 mg |
| Arginine | 3.00 mg |
| Magnesium stearate | 6.0 mg |
| Titanium dioxide | 5.00 mg |
| Talc | 15.00 mg |
| Glycerol | 5.00 mg |
| Total weight of the tablet | 1194.00 mg |

The amounts refer to the preparation of a standard industrial batch of 285.00 kg of tablets.

The tablets were prepared according to the procedure described in Example 1 using the components and amounts listed above.

TABLE 3

Batch 002 - core containing 400 mg of SAMe ion/tablet (qualitative/quantitative composition as in Example 2)

| Batch (T/t)[1] | Water Content % (K. Fischer) | AD[2] (%) | MTA[3] (%) | SAMe[4] |
|---|---|---|---|---|
| 002 (40/0) | 1.43 | 0.33 | 0.59 | 408.65 |
| 002A (40/1) | 1.36 | 0.78 | 0.65 | 406.48 |
| 002B (40/3) | 1.33 | 1.21 | 1.48 | 403.42 |

[1]Temperature (° C.)/time (months);
[2]adenosine;
[3]methylthioadenosine;
[4]SAMe sulfate p-toluensulfonate (mg/tablet);

The data in Table 3 show that the tablets have good stability.

Example 3

Tablets Containing 500 mg of SAMe Ion/Tablet

Composition Based on SAMe Sulfate p-Toluensulfonate

| SAMe sulfate p-toluensulfonate | 1000.00 mg |
|---|---|
| Core: | |
| Microcrystalline cellulose. | 50.0 mg |
| Magnesium hydroxide | 100.00 mg |
| Stearic acid | 120.00 mg |
| Magnesium stearate | 20.00 mg |
| Precipitated silica | 5.00 mg |
| Total weight of the core | 1295.00 mg |
| Coating: | |
| Shellac | 15.00 mg |
| Arginine | 3.00 mg |
| Magnesium stearate | 6.0 mg |
| Titanium dioxide | 5.00 mg |
| Talc | 15.00 mg |
| Glycerol | 5.00 mg |
| Total weight of the tablet | 1344.00 mg |

The amounts refer to the preparation of a standard industrial batch of 285.00 kg of tablets.

The tablets were prepared according to the procedure described in Example 1 using the components and amounts listed above.

TABLE 4

Batch 003 - core containing 400 mg of SAMe ion/tablet (qualitative/quantitative composition as in Example 2)

| Batch (T/t)[1] | Water Content % (K. Fischer) | AD[2] (%) | MTA[3] (%) | SAMe[4] |
|---|---|---|---|---|
| 003 (40/0) | 1.33 | 0.37 | 0.49 | 406.65 |
| 003A (40/1) | 1.32 | 0.79 | 0.75 | 405.44 |
| 003B (40/3) | 1.23 | 1.43 | 1.78 | 404.79 |

[1]Temperature (° C.)/time (months);
[2]adenosine;
[3]methylthioadenosine;
[4]SAMe sulfate p-toluensulfonate (mg/tablet);

The data in Table 4 show that the tablets have good stability.

Example 4

Tablets Containing 2 mg of (6S)-5-Methyltetrahydrofolic Acid, Glucosamine Salt/Tablet and 500 mg of SAMe Ion

| SAMe sulfate p-toluensulfonate | 1000.00 mg |
|---|---|
| (6S)-5-methyltetrahydrofolic acid, glucosamine salt | 2.38 mg |
| Core: | |
| Microcrystalline cellulose. | 140.0 mg |
| Mannitol | 100.00 mg |
| Stearic acid | 30.00 mg |
| Magnesium stearate | 20.00 mg |
| Precipitated silica | 5.00 mg |
| Total weight of the core | 1297.38 mg |
| Coating: | |
| Shellac | 15.00 mg |
| Arginine | 3.00 mg |
| Magnesium stearate | 6.00 mg |
| Titanium dioxide | 5.00 mg |
| Talc | 15.00 mg |
| Glycerol | 5.00 mg |
| Total weight of the tablet | 1346.38 mg |

The amounts refer to the preparation of a standard industrial batch of 285.00 kg of tablets.

The tablets were prepared according to the procedure described in Example 1 using the components and amounts listed above.

Example 5

Tablets Containing 2 mg of (6S)-5-Methyltetrahydrofolic Acid, Glucosamine Salt/Tablet

| | |
|---|---|
| (6S)-5-methyltetrahydrofolic acid, glucosamine salt | 2.38 mg |
| Core: | |
| Microcrystalline cellulose. | 140.0 mg |
| Mannitol | 100.00 mg |
| Stearic acid | 30.00 mg |
| Magnesium stearate | 20.00 mg |
| Precipitated silica | 5.00 mg |
| Total weight of the core | 297.38 mg |
| Coating: | |
| Shellac | 15.00 mg |
| Arginine | 3.00 mg |
| Magnesium stearate | 6.0 mg |
| Titanium dioxide | 5.00 mg |
| Talc | 15.00 mg |
| Glycerol | 5.00 mg |
| Total weight of the tablet | 346.38 mg |

The amounts refer to the preparation of a standard industrial batch of 300.00 kg of tablets.

Stability Tests on the Finished Product and Dissolution Profile

Both the stability at 40° C. and 75% RH (STRESS TEST) and the long term stability at ambient temperature (SHELF LIFE) of the compositions from Examples 1, 2, 3, obtainable according to the process of the invention, were evaluated based on the appearance changes (mainly colour variation), content (mg/tablet) in SAMe sulfate p-toluensulfonate and the increase of degradation products, mainly identifiable in adenosine and methylthioadenosine, expressed as percentage based on the mg of SAMe sulfate p-toluensulfonate per tablet, water content (K.F.) and changes in the dissolution profile over time by HPLC STRESS TEST.

The tablets were packed in Alu/Alu blisters in order to reproduce the final packaging conditions.

The samples thus prepared were stored for three months in a thermostated oven at a temperature of 40±2° C. e 75% RH.

Three samples from three different batches were used, and each batch was sampled after 0, 1, 3 and 6 months.

The results of the stress test are shown in the tables below (05-13).

TABLE 5

Batch 004- tablets containing 400 mg of SAMe ion/tablet (qualitative/quantitative composition as in Example 1)

| Batch (T/t)[1] | Water Content % (K. Fischer) | AD[2] (%) | MTA[3] (%) | SAMe[4] |
|---|---|---|---|---|
| 004 (40/0) | 1.65 | 0.58 | 0.58 | 408.65 |
| 004A (40/1) | 1.34 | 0.87 | 0.84 | 406.23 |
| 004B (40/3) | 1.43 | 1.73 | 1.89 | 405.54 |
| 004B (40/6) | 1.54 | 1.98 | 2.03 | 40.6 |

[1]Temperature (° C.)/time (months);
[2]adenosine;
[3]methylthioadenosine;
[4]SAMe sulfate p-toluensulfonate (mg/tablet);

TABLE 6

Batch 005 - tablets containing 400 mg of SAMe ion/tablet (qualitative/quantitative composition as in Example 1)

| Batch (T/t)[1] | Water Content % (K. Fischer) | AD[2] (%) | MTA[3] (%) | SAMe[4] |
|---|---|---|---|---|
| 005 (40/0) | 1.51 | 0.56 | 0.46 | 404.76 |
| 005A (40/1) | 1.42 | 0.78 | 0.65 | 406.65 |
| 005B (40/3) | 1.57 | 0.96 | 0.89 | 403.98 |
| 005C (40/6) | 1.39 | 1.97 | 1.56 | 402.01 |

[1]Temperature (° C.)/time (months);
[2]adenosine;
[3]methylthioadenosine;
[4]SAMe sulfate p-toluensulfonate (mg/tablet);

TABLE 7

Batch 006 - cpr 400 mg of SAMe ion/tablet (qualitative/quantitative composition as in Example 1)

| Batch (T/t)[1] | Water Content % (K. Fischer) | AD[2] (%) | MTA[3] (%) | SAMe[4] |
|---|---|---|---|---|
| 005 (40/0) | 1.51 | 0.56 | 0.46 | 404.76 |
| 005A (40/1) | 1.42 | 0.78 | 0.65 | 406.65 |
| 005B (40/3) | 1.57 | 0.96 | 0.89 | 403.98 |
| 005C (40/6) | 1.39 | 1.97 | 1.56 | 402.01 |

[1]Temperature (° C.)/time (months);
[2]adenosine;
[3]methylthioadenosine;
[4]SAMe sulfate p-toluensulfonate (mg/tablet);

TABLE 8

Batch 007 - tablets containing 400 mg of SAMe ion/tablet (qualitative/quantitative composition as in Example 2)

| Batch (T/t)[1] | Water Content % (K. Fischer) | AD[2] (%) | MTA[3] (%) | SAMe[4] |
|---|---|---|---|---|
| 007 (40/0) | 1.67 | 0.46 | 0.26 | 407.76 |
| 007A (40/1) | 1.52 | 0.88 | 0.74 | 407.00 |
| 007B (40/3) | 1.64 | 0.99 | 0.98 | 405.68 |
| 007C (40/6) | 1.76 | 2.09 | 1.96 | 400.00 |

[1]Temperature (° C.)/time (months);
[2]adenosine;
[3]methylthioadenosine;
[4]SAMe sulfate p-toluensulfonate (mg/tablet);

TABLE 9

Batch 008 - tablets containing 400 mg of SAMe ion/tablet
(qualitative/quantitative composition as in Example 2)

| Batch (T/t)[1] | Water Content % (K. Fischer) | AD[2] (%) | MTA[3] (%) | SAMe[4] |
|---|---|---|---|---|
| 008 (40/0) | 1.54 | 0.36 | 0.46 | 409.09 |
| 008A (40/1) | 1.76 | 0.77 | 0.88 | 405.80 |
| 008B (40/3) | 1.33 | 0.87 | 0.68 | 405.99 |
| 008C (40/6) | 1.66 | 2.29 | 1.56 | 403.02 |

[1]Temperature (° C.)/time (months);
[2]adenosine;
[3]methylthioadenosine;
[4]SAMe sulfate p-toluensulfonate (mg/tablet);

TABLE 10

Batch 009 - tablets containing 400 mg of SAMe ion/tablet
(qualitative/quantitative composition as in Example 2)

| Batch (T/t)[1] | Water Content % (K. Fischer) | AD[2] (%) | MTA[3] (%) | SAMe[4] |
|---|---|---|---|---|
| 009 (40/0) | 1.33 | 0.39 | 0.23 | 405.94 |
| 009A (40/1) | 1.77 | 0.79 | 0.74 | 403.70 |
| 009B (40/3) | 1.52 | 0.97 | 0.99 | 402.59 |
| 009C (40/6) | 1.48 | 2.03 | 1.93 | 400.22 |

[1]Temperature (° C.)/time (months);
[2]adenosine;
[3]methylthioadenosine;
[4]SAMe sulfate p-toluensulfonate (mg/tablet);

TABLE 11

Batch 010 - tablets containing 500 mg of SAMe ion/tablet
(qualitative/quantitative composition as in Example 3)

| Batch | Water Content % (K. Fischer) | AD[2] (%) | MTA[3] (%) | SAMe[4] |
|---|---|---|---|---|
| 010 (40/0) | 1.63 | 0.54 | 0.43 | 408.09 |
| 010A (40/1) | 1.37 | 0.55 | 0.84 | 406.94 |
| 010B (40/3) | 1.66 | 0.52 | 1.05 | 404.49 |
| 010C (40/6) | 1.72 | 2.53 | 1.89 | 403.42 |

[1]Temperature (° C.)/time (months);
[2]adenosine;
[3]methylthioadenosine;
[4]SAMe sulfate p-toluensulfonate (mg/tablet);

TABLE 12

Batch 011 - tablets containing 500 mg of SAMe ion/tablet
(qualitative/quantitative composition as in Example 3)

| Batch (T/t)[1] | Water Content % (K. Fischer) | AD[2] (%) | MTA[3] (%) | SAMe[4] |
|---|---|---|---|---|
| 011 (40/0) | 1.43 | 0.24 | 0.36 | 408.56 |
| 011A (40/1) | 1.55 | 0.65 | 0.78 | 407.82 |
| 011B (40/3) | 1.67 | 0.73 | 1.45 | 404.19 |
| 011C (40/6) | 1.82 | 2.11 | 2.34 | 402.72 |

[1]Temperature (° C.)/time (months);
[2]adenosine;
[3]methylthioadenosine;
[4]SAMe sulfate p-toluensulfonate (mg/tablet);

TABLE 13

Batch 012 - tablets containing 500 mg of SAMe ion/tablet
(qualitative/quantitative composition as in Example 3)

| Batch (T/t)[1] | Water Content % (K. Fischer) | AD[2] (%) | MTA[3] (%) | SAMe[4] |
|---|---|---|---|---|
| 012 (40/0) | 1.55 | 0.34 | 0343 | 407.63 |
| 012A (40/1) | 1.65 | 0.85 | 0.89 | 406.64 |
| 012B (40/3) | 1.47 | 0.92 | 1.25 | 405.39 |
| 012C (40/6) | 1.51 | 1.73 | 1.99 | 402.42 |

[1]Temperature (° C.)/time (months);
[2]adenosine;
[3]methylthioadenosine;
[4]SAMe sulfate p-toluensulfonate (mg/tablet);

Based on the stability data at 40° C. and 75% RH (stress test) it is possible to observe that all the batches examined after six months had suffered a degradation of about 5.0% in SAMe.

Based on the stability data at 40° C. and 75% RH (stress test) it is possible to observe that none of the batches undergo significant changes in the release profile of the active principle after 3 months storage at 40° C. and 75% RH with respect to time 0, with stability of the film during the stress test demonstrated (FIGS. 2 and 3).

Shelf Life The tablets were packed in Alu/Alu blisters in order to reproduce the final packaging conditions (usually Alu/Alu blister packs).

The samples were selected following the same rules and quantities described for the stress test, and stored in a thermostated environment at a temperature of 25±2° C. and humidity of 60% RH. Three samples from three different batches were used, and each batch was sampled after 0, 1, 3, 6 and 12 months.

The results of shelf life test are shown in the tables below (14-22).

TABLE 14

Batch 013- tablets containing 400 mg of SAMe ion/tablet
(qualitative/quantitative composition as in Example 1)

| Batch (T/t)[1] | Water Content % (K. Fischer) | AD[2] (%) | MTA[3] (%) | SAMe[4] |
|---|---|---|---|---|
| 013 (25/0) | 1.23 | 0.34 | 0.48 | 410.48 |
| 013A (25/3) | 1.43 | 0.74 | 0.73 | 410.23 |

TABLE 14-continued

Batch 013- tablets containing 400 mg of SAMe ion/tablet (qualitative/quantitative composition as in Example 1)

| Batch (T/t)[1] | Water Content % (K. Fischer) | AD[2] (%) | MTA[3] (%) | SAMe[4] |
|---|---|---|---|---|
| 013B (25/6) | 1.44 | 0.99 | 0.95 | 407.89 |
| 013C (25/12) | 1.23 | 1.53 | 1.89 | 405.36 |

[1]Temperature (° C.)/time (months);
[2]adenosine;
[3]methylthioadenosine;
[4]SAMe sulfate p-toluensulfonate (mg/tablet);

TABLE 15

Batch 014 - tablets containing 400 mg of SAMe ion/tablet (qualitative/quantitative composition as in Example 1)

| Batch (T/t)[1] | Water Content % (K. Fischer) | AD[2] (%) | MTA[3] (%) | SAMe[4] |
|---|---|---|---|---|
| 014 (25/0) | 1.54 | 0.42 | 0.48 | 409.44 |
| 014A (25/3) | 1.45 | 0.49 | 0.74 | 404.23 |
| 014B (25/6) | 1.66 | 0.69 | 0.99 | 406.49 |
| 014C (25/12) | 1.54 | 1.86 | 1.98 | 403.78 |

[1]Temperature (° C.)/time (months);
[2]adenosine;
[3]methylthioadenosine;
[4]SAMe sulfate p-toluensulfonate (mg/tablet);

TABLE 16

Batch 015 - tablets containing 400 mg of SAMe ion/tablet (qualitative/quantitative composition as in Example 1)

| Batch (T/t)[1] | Water Content % (K. Fischer) | AD[2] (%) | MTA[3] (%) | SAMe[4] |
|---|---|---|---|---|
| 015 (25/0) | 1.34 | 0.22 | 0.48 | 406.72 |
| 015A (25/3) | 1.77 | 0.47 | 0.73 | 405.93 |
| 015B (25/6) | 1.62 | 0.89 | 0.99 | 404.99 |
| 015C (25/12) | 1.64 | 2.05 | 1.83 | 403.06 |

[1]Temperature (° C.)/time (months);
[2]adenosine;
[3]methylthioadenosine;
[4]SAMe sulfate p-toluensulfonate (mg/tablet);

TABLE 17

Batch 016- tablets containing 400 mg of SAMe ion/tablet (qualitative/quantitative composition as in Example 2)

| Batch (T/t)[1] | Water Content % (K. Fischer) | AD[2] (%) | MTA[3] (%) | SAMe[4] |
|---|---|---|---|---|
| 016 (25/0) | 1.47 | 0.45 | 0.24 | 405.09 |
| 016A (25/3) | 1.36 | 0.84 | 0.44 | 404.83 |

TABLE 17-continued

Batch 016- tablets containing 400 mg of SAMe ion/tablet (qualitative/quantitative composition as in Example 2)

| Batch (T/t)[1] | Water Content % (K. Fischer) | AD[2] (%) | MTA[3] (%) | SAMe[4] |
|---|---|---|---|---|
| 016B (25/6) | 1.57 | 0.89 | 0.82 | 402.79 |
| 016C (25/12) | 1.48 | 1.87 | 1.79 | 400.36 |

[1]Temperature (° C.)/time (months);
[2]adenosine;
[3]methylthioadenosine;
[4]SAMe sulfate p-toluensulfonate (mg/tablet);

TABLE 18

Batch 017 - tablets containing 400 mg of SAMe ion/tablet (qualitative/quantitative composition as in Example 2)

| Batch (T/t)[1] | Water Content % (K. Fischer) | AD[2] (%) | MTA[3] (%) | SAMe[4] |
|---|---|---|---|---|
| 017 (25/0) | 1.23 | 0.56 | 0.48 | 409.02 |
| 017A (25/3) | 1.72 | 0.73 | 0.64 | 405.93 |
| 017B (25/6) | 1.23 | 1.05 | 0.98 | 407.29 |
| 017C (25/12) | 1.56 | 2.02 | 1.89 | 402.66 |

[1]Temperature (° C.)/time (months);
[2]adenosine;
[3]methylthioadenosine;
[4]SAMe sulfate p-toluensulfonate (mg/tablet);

TABLE 19

Batch 018 - tablets containing 400 mg of SAMe ion/tablet (qualitative/quantitative composition as in Example 2)

| Batch (T/t)[1] | Water Content % (K. Fischer) | AD[2] (%) | MTAD[3] (%) | SAMe[4] |
|---|---|---|---|---|
| 018 (25/0) | 1.45 | 0.22 | 0.58 | 408.44 |
| 018A (25/3) | 1.63 | 0.49 | 0.64 | 405.23 |
| 018B (25/6) | 1.62 | 0.69 | 0.85 | 403.85 |
| 018C (25/12) | 1.48 | 1.53 | 1.73 | 402.66 |

[1]Temperature (° C.)/time (months);
[2]adenosine;
[3]methylthioadenosine;
[4]SAMe sulfate p-toluensulfonate (mg/tablet);

TABLE 20

Batch 019 - tablets containing 500 mg of SAMe ion/tablet (qualitative/quantitative composition as in Example 3)

| Batch (T/t)[1] | Water Content % (K. Fischer) | AD[2] (%) | MTA[3] (%) | SAMe[4] |
|---|---|---|---|---|
| 019 (25/0) | 1.55 | 0.37 | 0.54 | 409.48 |
| 019A (25/3) | 1.36 | 0.65 | 0.84 | 407.28 |

TABLE 20-continued

Batch 019 - tablets containing 500 mg of SAMe ion/tablet
(qualitative/quantitative composition as in Example 3)

| Batch (T/t)[1] | Water Content % (K. Fischer) | AD[2] (%) | MTA[3] (%) | SAMe[4] |
|---|---|---|---|---|
| 019B (25/6) | 1.57 | 0.89 | 0.99 | 405.79 |
| 024C (25/12) | 1.48 | 1.99 | 1.89 | 402.36 |

[1]Temperature (° C.)/time (months);
[2]adenosine;
[3]methylthioadenosine;
[4]SAMe sulfate p-toluensulfonate (mg/tablet);

TABLE 21

Batch 020- tablets containing 500 mg of SAMe ion/tablet
(qualitative/quantitative composition as in Example 3)

| Batch (T/t)[1] | Water Content % (K. Fischer) | AD[2] (%) | MTA[3] (%) | SAMe[4] |
|---|---|---|---|---|
| 020 (25/0) | 1.34 | 0.62 | 0.38 | 406.42 |
| 020A (25/3) | 1.66 | 0.74 | 0.67 | 404.93 |
| 020B (25/6) | 1.82 | 0.89 | 1.09 | 402.49 |
| 020C (25/12) | 1.65 | 1.90 | 2.04 | 400.46 |

[1]Temperature (° C.)/time (months);
[2]adenosine;
[3]methylthioadenosine;
[4]SAMe sulfate p-toluensulfonate (mg/tablet);

TABLE 22

Batch 021- tablets containing 500 mg of SAMe ion/tablet
(qualitative/quantitative composition as in Example 3)

| Batch (T/t)[1] | Water Content % (K. Fischer) | AD[2] (%) | MTA[3] (%) | SAMe[4] |
|---|---|---|---|---|
| 021 (25/0) | 1.56 | 0.62 | 0.58 | 406.58 |
| 021A (25/3) | 1.46 | 0.73 | 0.84 | 407.13 |
| 021B (25/6) | 1.59 | 0.99 | 1.45 | 406.39 |
| 021C (25/12) | 1.49 | 1.93 | 2.23 | 407.96 |

[1]Temperature (° C.)/time (months);
[2]adenosine;
[3]methylthioadenosine;
[4]SAMe sulfate p-toluensulfonate (mg/tablet);

Based on the stability data at 25° C. and 60% RH (shelf life), it is possible to observe that all the batches examined after twelve months had suffered a very low SAMe degradation.

Based on the stability data at 25° C. and 60% RH (shelf life), it is possible to observe that none of the batches undergo significant changes in the release profile of the active principle after 12 months storage at 25° C. and 60% RH with respect to time 0, with stability of the film during the shelf life demonstrated.

The additional comparative examples reported below show that by replacing the magnesium stearate with another similar lipophilic excipient (stearic acid), commonly used in film-coating processes, the release profile significantly changes.

Comparative Example 1A

Tablets Containing 400 mg of SAMe Ion/Tablet

Composition Based on SAMe Sulfate p-toluensulfonate

| | |
|---|---|
| SAMe sulfate p-toluensulfonate or salts thereof | 800.00 mg |
| Core: | |
| Magnesium oxide | 40.0 mg |
| Magnesium hydroxide | 100.00 mg |
| Stearic acid | 120.00 mg |
| Magnesium stearate | 20.00 mg |
| Precipitated silica | 5.00 mg |
| Total weight of the core | 1085.00 mg |
| Coating: | |
| Shellac | 15.00 mg |
| Arginine | 3.00 mg |
| Stearic acid | 6.0 mg |
| Titanium dioxide | 5.00 mg |
| Talc | 15.00 mg |
| Glycerol | 5.00 mg |
| Total weight of the tablet | 1134.50 mg |

The process to obtain the core is identical to Example 1.

Tablet Film-Coating

Arginine and shellac are solubilised in water, in a container of appropriate size, to obtain a 20% w/v solution and, under continuous stirring, stearic acid, talc and silica are slowly added.

In another steel container, also equipped with a stirrer, sodium alginate is solubilised under vigorous stirring. The resulting suspension is poured into the solution of shellac, and the flask is rinsed with deionised water.

In the first coating step, the temperature of the cores is maintained at 48° C. for about 60 minutes, subsequently, and at regular intervals, it is lowered until it reaches a value of 44° C. in the final stage.

In the tablets thus produced, no increase in the water content percentage was observed. In addition, all the tests required by the quality specifications and the dissolution test, to verify the release profile over time, were performed on them.

Comparative Example 2A

Tablets Containing 400 mg of SAMe Ion/Tablet

Composition Based on SAMe Sulfate p-toluensulfonate

| | |
|---|---|
| SAMe sulfate p-toluensulfonate or salts thereof | 800.00 mg |
| Core: | |
| Microcrystalline cellulose | 100.0 mg |
| Magnesium hydroxide | 100.00 mg |
| Stearic acid | 120.00 mg |
| Magnesium stearate | 20.00 mg |
| Precipitated silica | 5.00 mg |
| Total weight of the core | 1145.00 mg |
| Coating: | |
| Shellac | 15.00 mg |
| Arginine | 3.00 mg |
| Stearic acid | 6.0 mg |

-continued

| | |
|---|---|
| Titanium dioxide | 5.00 mg |
| Talc | 15.00 mg |
| Glycerol | 5.00 mg |
| Total weight of the tablet | 1194.00 mg |

The amounts refer to the preparation of a standard industrial batch of 285.00 kg of tablets.

The tablets were prepared according to the procedure described in Example 1 using the components and amounts listed above.

Comparative Example 3A

Tablets Containing 500 mg of SAMe Ion/Tablet

Composition Based on SAMe Sulfate p-toluensulfonate or Salts Thereof

| | |
|---|---|
| SAMe sulfate p-toluensulfonate or salts thereof | 1000.00 mg |
| Core: | |
| Microcrystalline cellulose. | 50.0 mg |
| Magnesium hydroxide | 100.00 mg |
| Stearic acid | 120.00 mg |
| Magnesium stearate | 20.00 mg |
| Precipitated silica | 5.00 mg |
| Total weight of the core | 1295.00 mg |
| Coating: | |
| Shellac | 15.00 mg |
| Arginine | 3.00 mg |
| Stearic acid | 6.0 mg |
| Titanium dioxide | 5.00 mg |
| Talc | 15.00 mg |
| Glycerol | 5.00 mg |
| Total weight of the tablet | 1344.00 mg |

The amounts refer to the preparation of a standard industrial batch of 250.00 kg of tablets. The tablets were prepared according to the procedure described in Example 1 using the components and amounts listed above.

Comparative Example 4A

Dissolution Profile on the Finished Product

On the samples stored both at 40° C. and 75% RH (STRESS TEST) and at ambient temperature (SHELF LIFE) of the compositions from Examples 1A, 2A, 3A, obtainable according to the process of the invention, only the dissolution profile over time was evaluated by HPLC STRESS TEST.

The tablets were packed in Alu/Alu blisters in order to reproduce the final packaging conditions.

Stress Test

The samples thus prepared were stored for six months in a thermostated oven at a temperature of 40±2° C. and 75% RH Three samples from three different batches were used, and each batch was sampled after 0, 1, 3 and 6 months.

Figure 4:
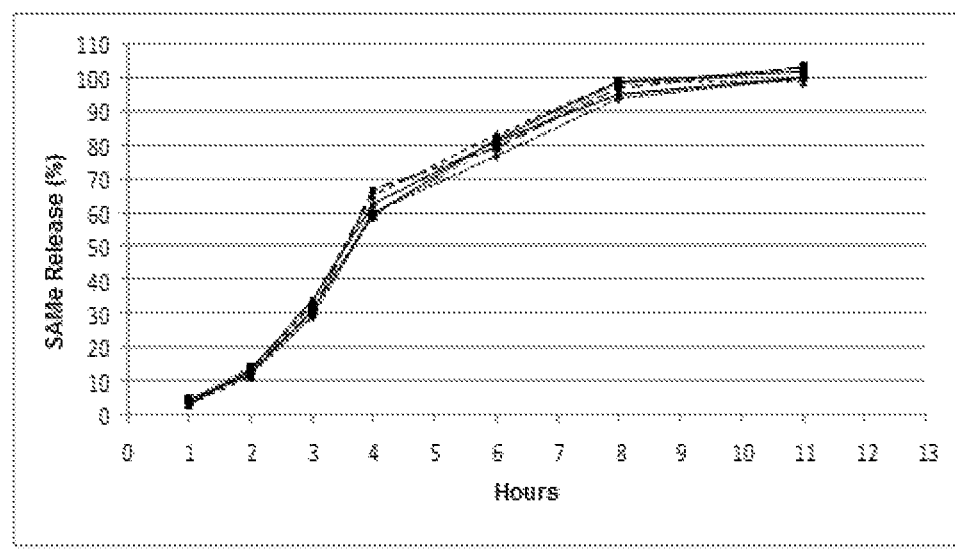
FIG. 4: Dissolution profile for 6 tablets of batch 022 at T=0 (stress test): 0-2 hours: gastric buffer pH 1.2; 2-12 hours: duodenal buffer pH 6.8

All the batches of the samples stored at 40±2° C. e 75% R.H (stress test) have a different release profile with respect to the same formulation with magnesium stearate instead of stearic acid (FIG. 4). Also in this case, they do not undergo significant changes in the release profile of the active principle after 12 months storage at 40±2° C. and 75% R.H, with stability of the film during the stress test demonstrated.

Shelf Life

The samples thus prepared were stored for twelve months in a thermostated oven at a temperature of 25±2° C. and a humidity of 60% RH.

Three samples from three different batches were used, and each batch was sampled after 0, 1, 3, 6 and 12 months.

The tablets were packed in Alu/Alu blisters in order to reproduce the final packaging conditions (usually Alu/Alu blister packs).

Figure 5:
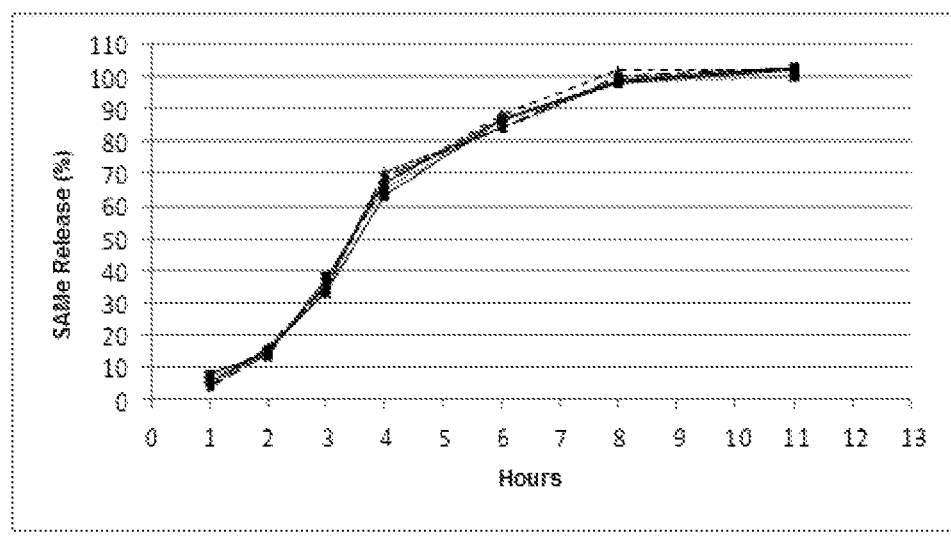
FIG. 5: Dissolution profile for 6 tablets of batch 025 at T=0 (shelf life): 0-2 hours: gastric buffer pH 1.2; 2-12 hours: duodenal buffer pH 6.8

All the batches of the samples stored at 25° C. and 60% RH (shelf life) have a different release profile with respect to the same formulation with magnesium stearate instead of stearic acid (FIG. 5). Also in this case, they do not undergo significant changes in the release profile of the active principle after 12 months storage at 25° C. and 60% RH, with stability of the film during the shelf life test demonstrated.

The invention claimed is:

1. A slow-release solid oral nutraceutical and/or pharmaceutical composition comprising:
    a) a core consisting of a donor of methyl groups and at least one pharmaceutically acceptable excipient, wherein said donor of methyl groups is selected from the group consisting of S-adenosyl-L-methionine (SAMe) or a pharmaceutically acceptable salt thereof and wherein the at least one pharmaceutically acceptable excipient is not calcium oxide, and
    b) an outer coating consisting of shellac and/or a pharmaceutically acceptable shellac salt thereof, magnesium stearate and at least one pharmaceutically acceptable excipient, wherein said at least one pharmaceutically acceptable excipient in b) is one or more of titanium dioxide, talc, glycerol, triethyl citrate, and sodium alginate,
    characterised in that the shellac and/or a pharmaceutically acceptable shellac salt thereof is present in the composition in an amount ranging between 1% and 5% by weight based on the total weight of the composition and characterised in that the magnesium stearate is present in the outer coating in an amount ranging between 10% and 20% by weight based on the total weight of the outer coating, and
    wherein the composition is characterized as having a zero order kinetic release profile with no more than 10% of the donor of methyl groups released in hours 1-2 and the remainder of the donor of methyl groups released in hours 3-11.

2. The composition according to claim 1, characterised in that said outer coating is a gastro-resistant coating.

3. The composition according to claim 1, characterised in that said SAMe pharmaceutically acceptable salt is selected from the group consisting of S-adenosylmethionine sulfate p-toluensulfonate, S-adenosylmethionine 1,4-butanedisulfonate, S-adenosylmethionine sulfate, S-adenosylmethionine tosilate, and S-adenosylmethionine phytate.

4. The composition according to claim 1, characterised in that said shellac salt is selected from the group consisting of arginine salt, ammonium salt, boron salt, and potassium salt.

5. The composition according to claim 1, characterised in that the outer coating results from application of shellac and/or pharmaceutically acceptable salt thereof in the form of a solution.

6. The composition according to claim 1, characterised in that SAMe or a pharmaceutically acceptable salt thereof is present in the composition in an amount ranging between 50% and 90% by weight based on the total weight of the composition.

7. The composition according to claim 1, characterised in that said solid oral composition is selected from the group consisting of a mixture, tablet, capsule, and granule.

8. A process for the preparation of a slow-release solid oral nutraceutical and/or pharmaceutical composition, comprising the following steps:
   a) mixing of a donor of methyl groups or a pharmaceutically acceptable salt thereof with at least one pharmaceutically acceptable excipient, wherein the at least one pharmaceutically acceptable excipient is not calcium oxide, and wherein said donor of methyl groups is selected from the group consisting of S-adenosyl-L-methionine (SAMe) or a pharmaceutically acceptable salt thereof;
   b) pre-compressing the mixture of a), followed by granulation of the pre-compressed mixture;
   c) mixing the granulated material of b) with at least one pharmaceutically acceptable excipient to form a solid oral formulation;
   d) film-coating the solid oral formulation of c) with an aqueous phase consisting of shellac and/or a pharmaceutically acceptable shellac salt thereof, magnesium stearate and at least one pharmaceutically acceptable excipient, wherein said excipient is one or more of titanium dioxide, talc, glycerol, triethyl citrate, and sodium alginate, said process being characterised in that the shellac and/or a pharmaceutically acceptable salt thereof is present in the nutraceutical and/or pharmaceutical slow-release solid oral composition in an amount ranging between 1% and 5% by weight based on the total weight of the composition and characterised in that the magnesium stearate is present in the outer coating in an amount ranging between 10% and 20% by weight based on the total weight of the outer coating and
   wherein the composition is characterized as having a zero order kinetic release profile with no more than 10% of the donor of methyl groups released in hours 1-2 and the remainder of the donor of methyl groups released in hours 3-11.

9. The process according to claim 8, characterised in that during the film-coating d), said solid oral formulation is maintained at a temperature ranging between 30° C. and 60° C.

10. The process according to claim 9, characterised in that said temperature is maintained for a period of time ranging between 10 minutes and 2 hours.

11. A method of imparting a prolong release characteristic to a pharmaceutical composition comprising a donor of methyl groups, comprising
    coating (a) a pharmaceutical composition consisting of (i) a donor of methyl groups and (ii) at least one pharmaceutically acceptable excipient, with (b) an outer coating consisting of shellac or a pharmaceutically acceptable shellac salt thereof, magnesium stearate, and at least one pharmaceutically acceptable excipient;
    wherein in (a) the donor of methyl groups is SAMe or a pharmaceutically acceptable salt thereof, and the at least one pharmaceutically acceptable excipient is not calcium oxide,
    wherein in (b) the at least one pharmaceutically acceptable excipient is one or more of titanium dioxide, talc, glycerol, triethyl citrate, and sodium alginate; and
    wherein said outer coating is characterised in that the shellac and/or a pharmaceutically acceptable shellac salt thereof is present in the composition in an amount ranging between 1% and 5% by weight based on the total weight of the composition and characterised in that the magnesium stearate is present in the outer coating in an amount ranging between 10% and 20% by weight based on the total weight of the outer coating and wherein the composition is characterized as having a zero order kinetic release profile with no more than 10% of the donor of methyl groups released in hours 1-2 and the remainder of the donor of methyl groups released in hours 3-11.

12. The composition according to claim 3, wherein the SAMe pharmaceutically acceptable salt is S-adenosylmethionine sulfate p-toluensulfonate or S-adenosylmethionine 1,4-butanedisulfonate.

13. The composition according to claim 4, wherein the shellac salt is an arginine salt.

14. The composition according to claim 5, wherein the solution is an aqueous solution or an alcoholic solution.

15. The composition according to claim 7, wherein the solid oral composition is a tablet.

* * * * *